US008677839B2

(12) United States Patent
Page et al.

(10) Patent No.: US 8,677,839 B2
(45) Date of Patent: *Mar. 25, 2014

(54) SURFACE SAMPLER FOR BIOLOGICAL PARTICLES

(75) Inventors: Andrew Edward Page, Smithton, MO (US); David Scott Alburty, Drexel, MO (US); Zachary A. Packingham, Drexel, MO (US); Pamela S. Murowchick, Lenexa, KS (US); Alec D. Adolphson, Raymore, MO (US)

(73) Assignee: InnovaPrep LLC, Drexel, MO (US)

( * ) Notice: Subject to any disclaimer, the term of this patent is extended or adjusted under 35 U.S.C. 154(b) by 574 days.

This patent is subject to a terminal disclaimer.

(21) Appl. No.: 12/814,972

(22) Filed: Jun. 14, 2010

(65) Prior Publication Data

US 2010/0313685 A1    Dec. 16, 2010

Related U.S. Application Data

(60) Provisional application No. 61/268,385, filed on Jun. 12, 2009.

(51) Int. Cl.
*G01N 1/00* (2006.01)

(52) U.S. Cl.
USPC .......................................................... 73/863

(58) Field of Classification Search
USPC ............... 73/863, 864, 864.51, 864.91, 60.11
See application file for complete search history.

(56) References Cited

U.S. PATENT DOCUMENTS

| 3,751,755 | A | * | 8/1973 | Smith | 15/302 |
| 4,974,618 | A | * | 12/1990 | Nysted | 134/21 |
| 2001/0041352 | A1 | * | 11/2001 | Reilly et al. | 435/34 |
| 2003/0019068 | A1 | * | 1/2003 | Field et al. | 15/320 |
| 2003/0070250 | A1 | * | 4/2003 | Roy et al. | 15/327.5 |
| 2007/0039123 | A1 | * | 2/2007 | Bird | 15/345 |

* cited by examiner

*Primary Examiner* — Peter Macchiarolo
*Assistant Examiner* — Tamiko Bellamy
(74) *Attorney, Agent, or Firm* — Moazzam & Associates, LLC (57) ABSTRACT

Novel rapid, efficient sample collection systems, devices and methods are disclosed which remove and capture particles, and especially biological particles from surfaces into a liquid sample. The devices were developed primarily for obtaining samples of biological contamination from environmental surfaces. Biological particles, as described here, include bacteria, viruses, and other microorganisms, and other particles of biological origin including nucleic acids, proteins, and toxins.

16 Claims, 6 Drawing Sheets

SURFACE SAMPLER FOR BIOLOGICAL PARTICLES

This U.S. Utility Patent Application claims priority to U.S. Provisional Patent Application Ser. No. 61/268,385, filed Jun. 12, 2009, the content of which is hereby incorporated by reference in its entirety into this disclosure.

BACKGROUND OF THE INVENTION

1. Field of the Invention

The present invention relates to surface samplers. More specifically, the present invention relates to two dimensional and three dimensional surface samplers for biological particles.

2. Background of the Invention

In today's world, there has become an increased interest and understanding in contaminants that rest or reside on surfaces of virtually everything that comes into contact with humans. These include contaminants on food or counter surfaces, door handles, shopping cart handles, and countless other surfaces which are frequently in contact with human hands or bodies. Such contaminants are typically biological in the form of viruses or bacteria or other harmful particles. To that effect, a number of surface sampling procedures have been developed to test for contamination and other surface pathogens that may be present on a variety of surfaces.

Most conventional surface sampling has been conducted using swabs, wipes or cloth. In some instances, filter material is used for swabbing. Most result in a sample that is picked up on a moistened surface and must be extracted into a liquid for analysis.

In most common tests, cotton swabs (e.g., Q-tips) are used to sample the surface, then the swabs are placed into a tube. Next a conventional procedure is followed to recover particles from that sample into a liquid. Once in liquid, there is an attempt to identify what is collected from that surface via analysis through viable culture, PCR or other methods.

Although such conventional techniques are useful, they are not without their problems and limitations. There are a number of problems with conventional techniques, a main problem being a very limited surface sample. Further, the removal efficiency is low from certain surfaces, and the results are also very dependent on how careful the user is in terms of swabbing the surface.

Further common testing techniques include use of a sponge, or sponge-type surface sampler. The sponge is used to swab the surface, and is about a few inches in diameter so it allows the collection from a larger surface area. The sponge may be used dry or wet. In some techniques, there is a bottle associated with the backside of the sponge which squeezes the liquid through it and draws the collected particles out from that surface and typically into a collection sample bottle, which is then sealed for transport and analysis. One of the primary disadvantages of this sponge technique is that there is lower efficiency from recovering the particles from the surface using the sponge and lower efficiency for recovering the particles back out of the sponge (which naturally has cells in which particles may imbed within). Again, like the swab method, there is a lot of potential variability due to how the user does the extraction from the surface and the extraction from the sponge.

Other conventional techniques used for surface sampling include a large and heavy pressure washing system using a showerhead-like wand which sprays a liquid from a center nozzle and then collects the liquid in a ring of apertures around a peripheral surface of the wand. The jet from the surface is allegedly able to remove particles from the surface which are then drawn up through a vacuum port which goes into the collection container. Although with its advantages, the spray system is extremely heavy (approximately 200 pounds), and is difficult to move freely, and is dependent on the volume of liquid sprayed onto the surface and subsequently collected by the vacuum.

What is needed is an efficient and effective system, device, and method to test the two or three dimensional surface of virtually any object, and subsequently collect the samples from the surface in a manner which produces high concentration of surface sample product. The system, device, and method should be simple to use and administer, inexpensive to manufacture, and effective at collecting and sampling from any surface.

SUMMARY OF THE INVENTION

A novel surface and object sample extraction device, system and method are disclosed which use a "wet foam" method. The surface sampler and object extractor embodiments described herein offer significant advantages over previous methods of biological particulate matter samplers including swabs, wipes, sponges and spray wash methods described above. Like swabbing, wiping, sponging, and spray washing and the other known conventional methods, the present invention extracts the sampled particles from the surface being sampled prior to analysis, but with many advantages: 1) The liquid volume of the sample produced per unit area sampled is reduced because the wet foam used to extract the particles from the surface quickly collapses to a fraction of its original volume upon collection. 2) This method is more efficient at removing particles from the sampled surfaces, resulting in collected fluid with a proportionally higher concentration of target particles, allowing better detection in devices such as multi-well plate readers that utilize small input samples. 3) This device is much more readily adapted to automated systems than hand operated swabbing and sponging techniques 4) This surface sampling method enables the construction of smaller, lighter-weight portable surface to liquid samplers because the "wet foam" extraction fluid is supplied to the spray nozzle under gas pressure, rather than mechanical pumps. The only electrically powered circuit in the device, the vacuum sample pickup, can be battery operated. This enables the sampler to be easily carried up steps, ladders, taken to sampling locations by first responders, and operated for long periods of time without operator fatigue. In the backpack configuration discussed in this disclosure, the sampler can be carried by a person wearing full MOPP gear or other protective gear. 5) This surface sampling method allows a larger area to be sampled per unit time and per sample than swabs, wipes, and sponges because a larger volume of sampling fluid can conveniently be supplied by a rechargeable/refillable extraction fluid tank. This advantage improves the probability of detection. 6) Shear produced in the thin film of bubbles in the "wet foam" extracts particles more efficiently than other methods. 7) Use of added mechanical force such as megasonic or ultrasonic waves to increase shear can further increase sample extraction efficiency. 8) The suction wand of the surface sampler can be used to sample a large volume of standing liquid if it is present on the surface being sampled. 9) Fabric can be efficiently sampled because the wet foam spray penetrates the fibers with extraction fluid and the vacuum suction pulls a large fraction of the sample back out of the fibers. When the wet foam is applied to one side of the fabric or porous material and the vacuum is applied to the opposite side, collection efficiency is further improved for certain applications.

The present invention presents novel, rapid, efficient sample collection devices and methods that remove and capture particles, and especially biological particles, from surfaces into a liquid sample. The present invention was developed primarily for obtaining samples of biological contamination from environmental surfaces. The surfaces may be substantially flat (two dimensional), or contoured (three dimensional). Biological particles, as described here, include bacteria, viruses, and other microorganisms, and other particles of biological origin including nucleic acids, proteins, and toxins.

Collection of these particles as described here is advantageous for detection of target particles such as pathogens because capture in a liquid allows many detection and identification methods to be used. Detection of pathogens and spoilage organisms on surfaces is advantageous for the prevention of the spread of further contamination and resulting illness. Collection in a liquid also allows concentration of the captured particles into a small volume, which makes them easier to detect. Biological materials that are suspended or dissolved in the liquid are also captured and can subsequently be identified if desired.

In one exemplary embodiment, the present invention is a system for extracting particles from a surface. The system includes a source of pressurized liquid containing a liquid; a source of gas containing a liquid soluble gas, wherein the source of gas is connected to the source of pressurized liquid such that the gas is dissolved into the liquid; an extraction device including an outlet port wherein the pressurized liquid having gas dissolved therein is applied as a wet foam to a surface having particles thereon and an inlet port wherein the wet foam is extracted from the surface; and a liquid collection reservoir in connection with the inlet port, wherein the wet foam extracted by the inlet port is stored as liquid having particles therein within the collection reservoir.

In another exemplary embodiment, the present invention is a method for extracting particles from a surface. The method includes providing a source of pressurized liquid; providing a source of gas, wherein the gas is connected to the pressurized liquid such that the gas is dissolved into the liquid; applying a wet foam on the surface having particles, the wet foam formed by the gas dissolved in the pressurized liquid being exposed to ambient pressure; extracting the wet foam from the surface; and collecting the wet foam as liquid within a reservoir.

DETAILED DESCRIPTION OF THE INVENTION

The present invention provides novel devices, systems and methods for collecting and measuring surface samples in an efficient and effective manner. The present invention provides many advantages over conventional systems including, but not limited to, allowing the capture of surface particles with high sampling efficiency resulting in high concentrations in a relatively low volume of liquid.

The present invention uses a collection fluid previously developed by the inventors, and described in co-pending and co-owned U.S. Published Patent Application Serial Number US 2009/0101575, described herein and throughout this disclosure as "wet foam" and which application is incorporated by reference herein into this disclosure in its entirety. This novel collection fluid ("wet foam") is created by dissolving a compressed gas in a chemically buffered fluid containing a foaming agent and subjecting the fluid to a pressure drop. Further details of the production of such wet foam is described in the above identified application and is incorporated by reference into the present disclosure.

The wet foam described above is applied from a pressurized tank to the surface to be extracted through a constricted nozzle, or orifice, that applies the fluid with some force onto the surface within an area that is physically constrained such that the formed wet foam can then be picked up by suction and transferred to a sample collection vessel. This method of surface extraction enables the construction of a smaller, lighter sampling device than is possible using pumps to force extraction fluid onto the surface being sampled, since compressed gas is the pressure source instead of batteries, motors, and mechanical pumps. Additionally, wet foam surface extraction produces final samples with smaller final volumes than is possible with plain liquid.

Use of the wet foam with the present invention reduces the need of liquid volume to about one fifth of that with liquid alone, as used with other conventional systems, thus allowing one to collect surface particles into a much smaller volume. This is an important advantage as collection of particles of interest into a fifth of the volume provides the ability to detect about $\frac{1}{5}^{th}$ the number of particles as compared to detection of particles from surfaces sampled with other "pure liquid" conventional surface sampler systems. Another advantage of the present invention is that since less volume liquid needs to be used, a higher spray force may be used, resulting in a greater particle sample release from the surface, without having to use additional liquid volume. Further, there are other advantages with use of the foam, one being that the foam is very viscous compared to an aqueous liquid. The increased viscosity allows it to sweep across the surface inside of the head acting as a solid slush sweeping across the surface rather than just turbulence at the point of impact, so it's effective at removing substances from a surface over a distance as it travels from the point of injection to the point of collection.

Use of the wet foam with the present system and method provides a novel, efficient and effective manner of obtaining samples from any surface. Such wet foam is created in part by pressurizing the liquid under carbon dioxide and then releasing it into the atmosphere's pressure. The gas is typically carbon dioxide, and once the foam gets exposed to atmospheric pressure, the gas escapes from the foam and the foam goes back into liquid again which allows the user to proceed onto the next step of analysis without having to deal with the foam at that point because it has already turned back to a liquid sample. The foam used in the current invention allows use of about 20% of the liquid volume than conventional systems, which percentage is dependent on the carbon dioxide pressure that the liquid is held under before it is released.

Although carbon dioxide is being used as the gas herein and through the examples in this disclosure, other gases may also be used, including but not limited to, nitrous oxide, argon or other inert gases. The reason that carbon dioxide is used is because it's very soluble in water at room temperature, thereby allowing the expansion of about five times in foam form, because at room temp and about 120 PSI, one volume of liquid can hold about five volumes of carbon dioxide.

The hand held wand or nozzle that is being used is shown in the examples as similar to a paint sprayer nozzle, so it actually spreads out the wet foam as a fan approximately an inch and a half wide, or less. The wet foam reacts with the surface for about an inch (maybe even a little more) before it's drawn up into a vacuum port. So the user slides it in one direction. When the invention is in use, the user starts out by placing the wand on the surface, turning on the vacuum pump, then turning on the spray nozzle and then starting pushing it in the direction of the spray nozzle, so essentially pushing the foam back up into the vacuum port.

Another novel aspect of the present invention allows for maintaining the sample collection viable itself, by collecting the sample in a cyclone system. This allows the user to have the particle laden fluid spinning around the outside edge of the interior of the cyclone such that the vacuum that picks up the collected foam is pulled without losing the sample through the fan or through the blower essentially. Conventional systems do not have this feature, and typically use a hydrophobic filter attached to a collection reservoir, such that the vacuum is pulled through the hydrophobic filter preventing loss of sample. Among the disadvantages of this type of system include that the hydrophobic filters easily become blinded when too much fluid comes in contact with them and particles of interest are readily lost onto the filter surface. Thus, the present invention provides further improvements over the conventional systems.

Another advantage of the present invention is that to create the wet foam, a surfactant must be included in the liquid, and no filters are used. Conventional systems typically use a hydrophobic filter. Use of the cyclone in the present invention eliminates the need for use of a hydrophobic filter. Use of the surfactant increases the efficiency of the collection. It's possible that use of a surfactant in other conventional filter-based systems would clog up the system by wetting the filter and cause the vacuum flow through the system to stop. In one embodiment of the present invention a hydrophobic filter may be used in combination with the cyclone to eliminate the potential for aerosolization of potentially dangerous particles into the ambient air. In this way the cyclone acts as a liquid knockout upstream of the hydrophobic filter to eliminate the potential for liquid to reach the filter, thus removing the possibility of wetting out of the filter.

Considering the above described features and advantages, a more detailed analysis of the individual components of exemplary systems according to the present invention may be made. Such exemplary embodiments are presented in the accompanying drawings. For the following description, it can be assumed that most correspondingly labeled structures across the figures (e.g., 132, 232 and 332, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1 shows a schematic of a surface extraction system 100 according to an exemplary embodiment of the present invention. The system 100 uses an extraction fluid stored within an extraction fluid reservoir 120 and held under a constant head pressure with a water soluble gas. The pressurized fluid 122 travels through conduit 121 and is released to an extraction wand 110 by opening a valve 115, thereby allowing the fluid to escape through an aperture 125, which can be a spray nozzle or orifice. The wand 110 can be in various shapes as recognized by one having ordinary skill in the art. In the embodiment shown, the wand 110 has a head portion 111 and a handle portion 112. Upon passing through the orifice 125, which can be a nozzle, the extraction fluid forms a wet foam 151, as gas escapes from the fluid, forming small bubbles within the fluid. When the pressurized extraction liquid gets to the nozzle 125, it goes through a constriction so on one side there is high pressure and as it goes through the nozzle 125 it goes quickly to ambient pressure. For example, if the pressurized fluid is held at 250 psi, and goes through the nozzle 125, it immediately drops down to ambient pressure (about 14.7 psi) and that quick pressure drop causes all of the carbon dioxide that is dissolved in the extraction fluid to expand and come out of the solution and create the microbubbles, thereby generating the wet foam. The wet foam then impacts the volume within a space 152 enclosed on the top and three to four sides by the wand and on the bottom by the sampling surface 150. The wet foam 151 then rapidly reacts along the surface 150 before being picked up with a vacuum source opening 126.

The system 100 is operated by turning on the vacuum source 135 and then opening the wet foam valve 115 while holding the extraction wand 110 to the surface 150. The wand 110 is then moved forward 161 or backward at a moderate pace thereby scrubbing the surface with the foam 151 which is continuously picked up by vacuum source 135, which effects the vacuum on the sample reservoir 130 through conduit 136. The recovered fluid 112 is pulled through conduit 131 and captured into a cyclonic sample collection reservoir 130.

The pressurized fluid reservoir 120 is used to hold a volume of an extraction fluid under a head pressure of a water soluble gas. Appropriate gases include, but are not limited to, carbon dioxide, nitrous oxide, and other water soluble gases. Head pressures are generally in the range of 20 psi to as much as 900 psi, or more preferably, in the range of 50 to 600 psi. The extraction fluid contains a surfactant, protein, or other foaming agent in a concentration sufficient to produce a high quality wet foam, but in a sufficiently low concentration so as to allow the foam to break down relatively quickly and to not be inhibitory to subsequent analysis. Foaming agent concentrations are highly dependent on the agent being used. Foaming agents include, but are not limited to, Tween 20, Tween 80, Triton X-100 (and other alternative Triton and Tween formulations), microbial and viral growth media, bovine serum albumin, and ovalbumin. Concentrations of Tween and Triton concentrations generally fall between 0.001% and 1.0%, and more preferably in the range of 0.01% and 0.5%. Combining foaming agents, such as Tween 80 and microbial growth media, are advantageous in some applications to increase efficiency and improve compatibility with analysis methods and for increasing target particle culturability. Buffer, including phosphate buffered saline, tris buffer, PBS, or other buffer to buffer against carbonic acid being formed (when exposed to carbon dioxide), may be added to the extraction fluid to maintain a relatively neutral pH. Without the addition of the buffer the fluid generally becomes acidic due to carbonic acid (when using carbon dioxide as the expansion gas). Salts, small particles, and other additives may also be added to improve the ability of the wet foam to extract surfaces, improve culturability, or improve compatibility with analysis methods.

Figure 1:
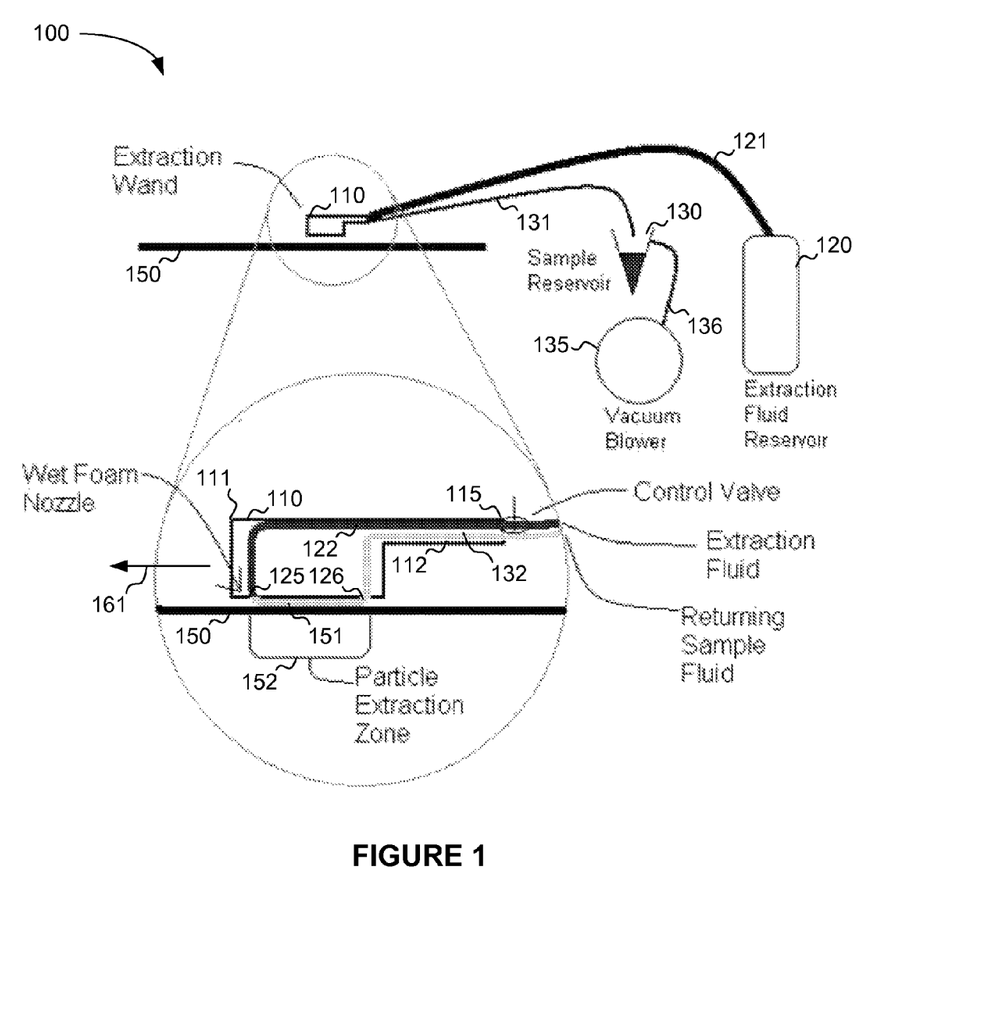
FIG. 1 shows a general surface sampling system, according to an exemplary embodiment of the present invention.

In certain exemplary embodiments, the pressurized fluid reservoir 120 is precharged with pressurized fluid or alternatively it may contain an integral bubbler which is attached to a regulated gas cylinder to charge the fluid with a water soluble gas. In certain exemplary embodiments, the precharged reservoirs use a quick connect and can be readily attached or detached from the surface extraction system. A length of tubing 121 attaches the pressure reservoir 120 to the extraction wand 110. Within the extraction wand 110 a push button, toggle valve, or electronically controlled on/off valve 115 is used to start and stop the dispensing of the extraction fluid 122. A separate switch controls a HEPA filtered blower 135 that is used to capture the dispensed wet foam 151 into a cyclonic sample collection reservoir 130.

Figure 2:
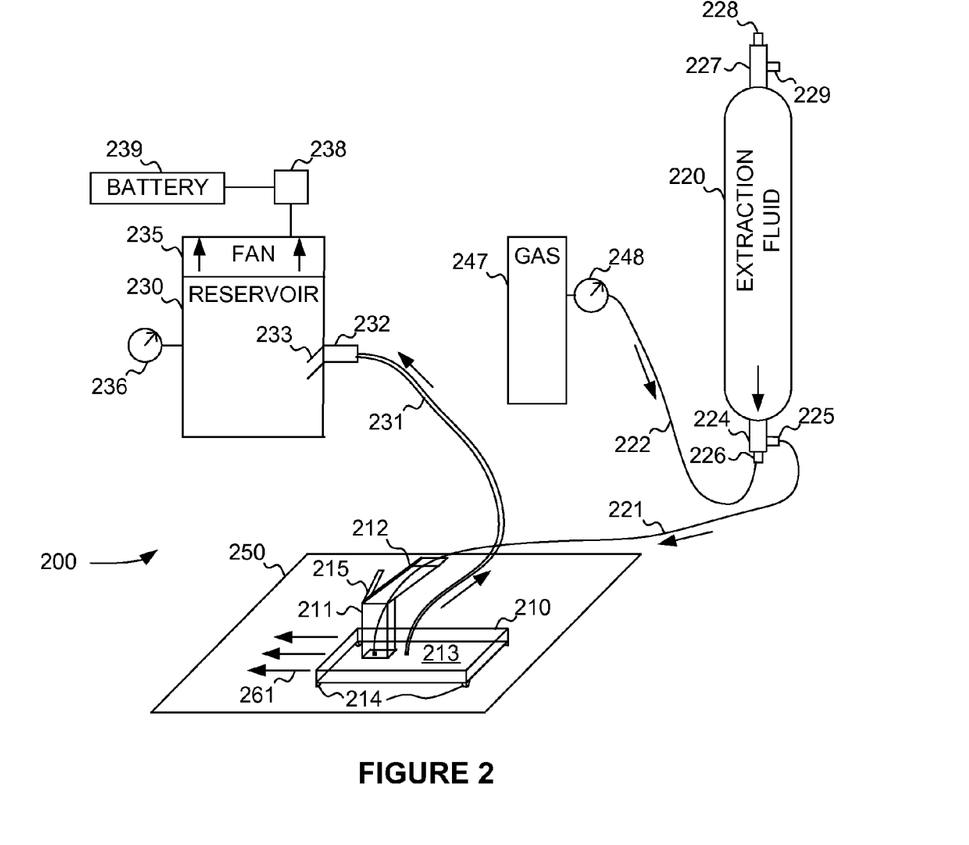
FIG. 2 shows a two dimensional surface sampling system in detail, according to an exemplary embodiment of the present invention.

As shown in FIG. 2, a more detailed diagram of a surface extraction system 200 is presented. In this system 200, extraction fluid is stored in a sealed and pressurized container 220, which further includes fill 228 and purge 229 ports in a first port extension 227. A gas source 247 supplies pressurized gas as monitored and controlled through a pressure gauge 248. The gas is preferably carbon dioxide, but may be other gases as described above. Gas is directed to the extraction fluid through a second port extension 224 through gas inlet port 226. Mixed fluid and gas are then directed through the second port extension 224 through output port 225 and through conduit 221 to extraction wand 210. Extraction wand 210 includes a head portion 211 and a handle portion 212. A trigger or valve 215 allows the operator to turn on/off the system through manual pressure. Extraction wand 210 includes body portion 213 which is attached to top portion 211. Body portion 213 includes bottom spacers 214 which create a designated space between the bottom portion of the body portion 213 and a surface 250. A sample reservoir 230 in a generally circular cylindrical shape is designed to receive extracted fluid from the extraction wand 210 through conduit 231. As extraction wand 210 is moved in the direction indicated by the arrows 261, wet foam in contact with the surface 250 is extracted as fluid which enters cylindrical reservoir 230 through inlet port 232 and internal directional port 233 which, in conjunction with the inlet force of the fan 235, create a cyclone within cylindrical reservoir 230. The fan is powered through battery 239 (or other power source) and controlled by power switch 238. Pressure gauge 236 helps ensure that the pressure within cylindrical reservoir 230 is such that a proper cyclone flow is created therein by having fluid enter and cyclone through and to the bottom of reservoir 230.

Figure 3A:
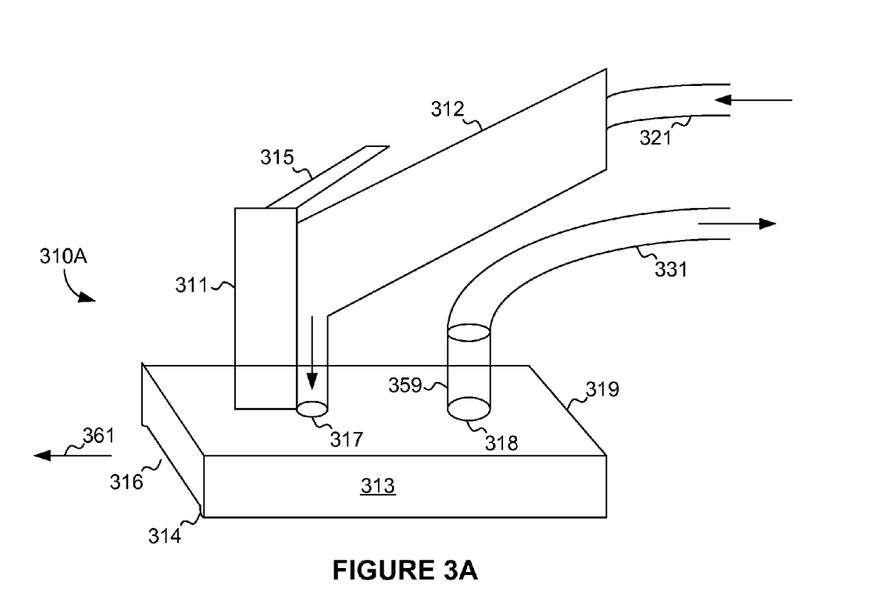
FIG. 3A shows a surface sampling device, according to an exemplary embodiment of the present invention.
Figure 3B:
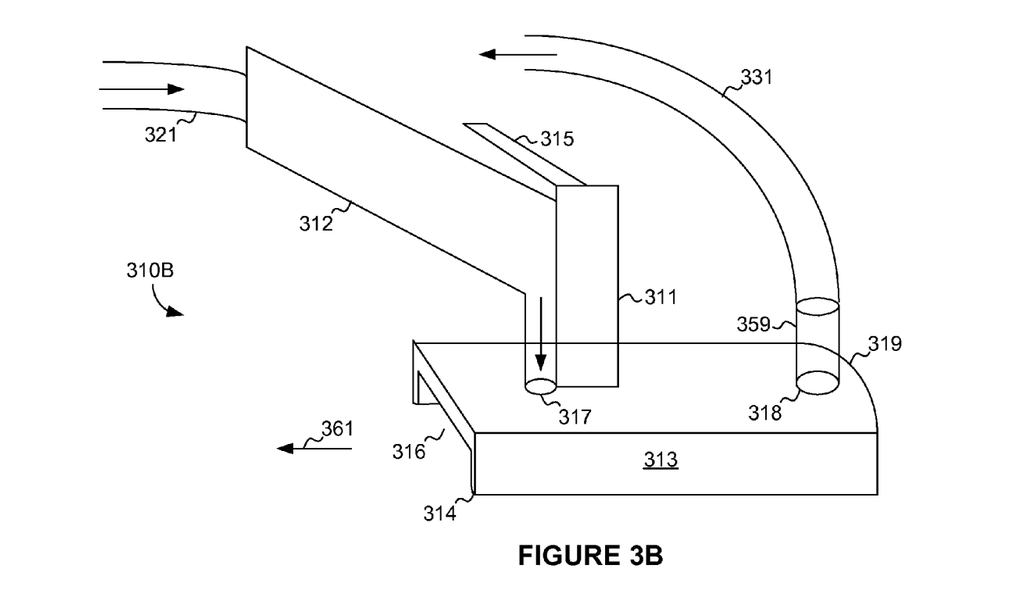
FIG. 3B shows another surface sampling device, according to an exemplary embodiment of the present invention.

FIGS. 3A and 3B show variations in the shape of extraction wands 310A and 310B, respectively, according to certain exemplary embodiments of the present invention. The extraction wands 310A and 310B include top portions 311 and handle portions 312. Trigger valves 315 control the inflow of extraction fluid through conduit 321 into extraction wand 310 and onto a surface through aperture 317 in body portion 313. The wet foam produced and exposed to the surface is contained within surface contact volume 316 as formed and determined by spacers 314, bottom of body portion 313 and a surface (not shown). Extraction wand 310A has smaller spacers 314 than extraction wand 310B, thereby producing a smaller surface contact volume 316. As the extraction wand 310A or 310B exposes the surface to extraction fluid, conduit 331 draws in the wet foam as extracted liquid from surface contact volume 316 through aperture 318 and adapter 359 and into conduit 331.

The shape of body portion 313 may vary in different embodiments of the extraction wand. In extraction wand 310A, shown in FIG. 3A, body portion 313 has a straight edge 319, and has a configuration such that the extraction wand 310A is moved from a right to left direction 361 in order to dispense and then collect the wet foam as extracted fluid. In extraction wand 310B, shown in FIG. 3B, body portion 313 has a rounded edge 319, and has a configuration such that the extraction wand 310B is moved from a right to left direction 361 in order to dispense and then collect the wet foam as extracted fluid. Thus, extraction wand 310A operates in a "push" motion with respect to handle 312 position when collecting extracted fluid, and extraction wand 310B operates in a "pull" motion with respect to handle 312 position when collecting extracted fluid. However, both embodiments of the extraction wand 310A and 310B would operate in both push and pull directions during use. Further, although the extraction wand and nozzle have been shown with a given shape and geometry, it would be evident to one having ordinary skill in the art that they can have other shapes and configurations to account for different types of surfaces, including but not limited to, carpet, rubber surfaces, asphalt or concrete or walls, and so on. Other configurations of the extraction wand are also possible and within the scope of the present invention as understood by one having ordinary skill in the art after consideration of the present disclosure.

Figure 4:
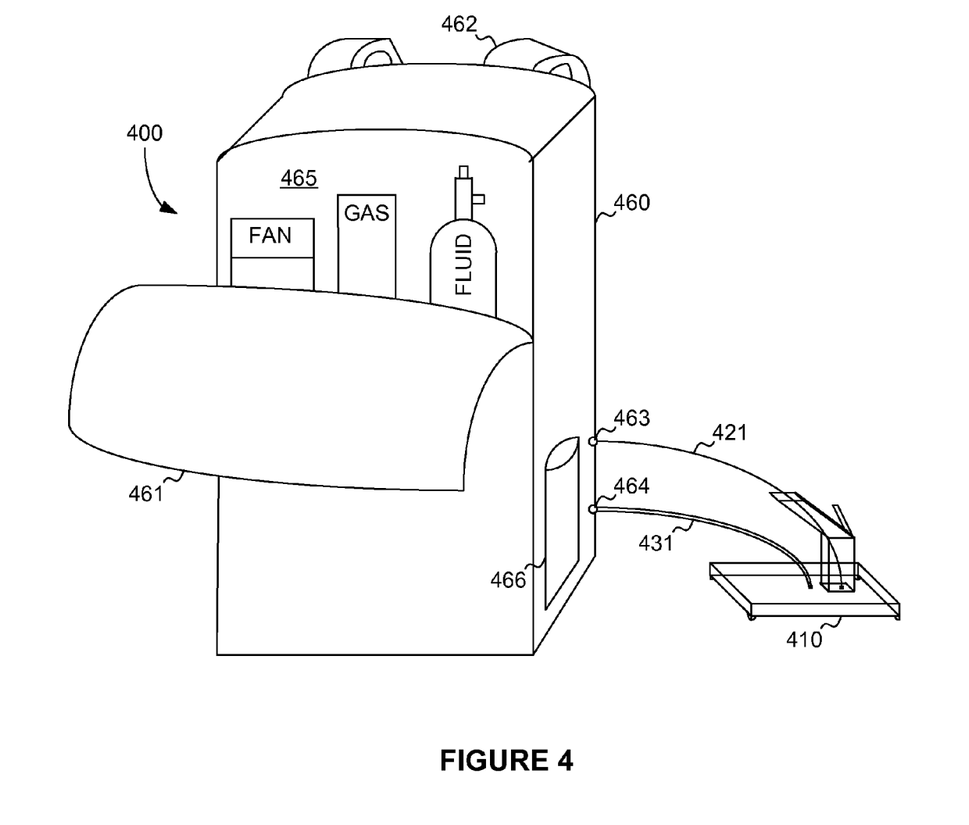
FIG. 4 shows a portable two dimensional surface sampling system, according to an exemplary embodiment of the present invention.

One of the many features and advantages of the present invention is that it is highly portable, as shown in the exemplary 15-20 lb portable system 400 in FIG. 4. An exemplary configuration of the surface extraction system (as shown in, for example, FIG. 2 as system 200) fits within an interior space 465 of a small backpack 460. The cover 461 of the backpack 460 may be opened to replace/repair elements or collect the extracted fluid. Alternatively, the extracted fluid can be collected through a valve and tube running through the bottom or side panel of the backpack. The extraction wand 410 may be external to and connect to the backpack 460 by a flexible bundle containing the fluid hose 421 (through port 463), vacuum hose 431 (through port 464), and wiring for the vacuum switch. The user wears the backpack during use using shoulder straps 462 or other carrying straps. A section of a surface to be extracted is identified and may be outlined by marking the boundaries if appropriate. The extraction wand 410 is grasped in one hand and the vacuum on/off switch is activated. The wand 410 is held to the surface to be extracted and the foam valve is activated. The user then moves the extraction wand 410 forward at a rate of approximately 5 seconds per foot. Each pass of the wand 410 extracts a section approximately 2 inches wide. At the end of each pass the foam valve is deactivated and the wand 410 is placed at the start of a new sampling section. It is important to overlap sampling sections to ensure that the entire area is collected. When the entire section has been sampled the foam valve is deactivated and the wand 410 is passed back over the entire sampled area to capture residual fluid. When the sampling area is relatively dry, the vacuum switch is turned off. The wand 410 may then be placed into an external holster or holding pouch 466 for easy access later. The fluid can then be drained to an appropriate sample container and prepared for analysis. It is most common to first concentrate the sample in a conventional concentrator system prior to analysis. In other embodiments, it may be possible to incorporate the concentrator and add a further analyzer into the backpack 460 as well.

Cleaning and decontamination of the sampler can be performed using standard procedures, including, for example, 3% hydrogen peroxide or 0.5% sodium hypochlorite (10% dilution of commercially available bleach) or other common means of disinfection.

Figure 5:
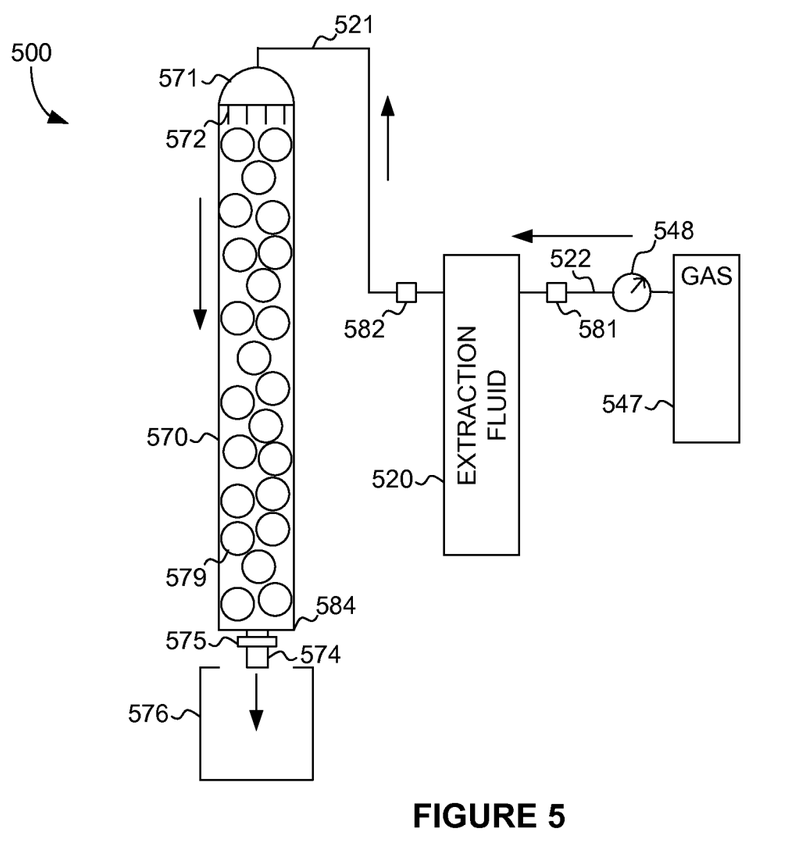
FIG. 5 shows a three dimensional surface sampling system, according to an exemplary embodiment of the present invention.

FIGS. 1-4 have shown various embodiments for sampling surfaces with substantially flat or two dimensional planar surfaces. The present invention is not limited to such surfaces, however, and may also be used to sample three dimensional or (non-flat) contoured surfaces. The exemplary surface extraction system 500 shown in FIG. 5 is used to sample contoured surfaces. Extraction fluid is contained within pressurized reservoir 520 which is under pressure by a source of gas 547 under control of a pressure regulator 548 and valve 581. Gas from the gas source 547 is directed to extraction fluid reservoir 520 through conduit 522 to produce a pressurized gaseous liquid. Control valve 582 controls the flow of gaseous liquid (wet foam) through conduit 521 to sample testing chamber 570. A wet foam distributor 571 acts similar to a shower head to produce multiple streaming sources 572 of wet foam onto the surfaces of one or more objects 579. Such objects can be anything whose surface contain particles which are intended to be detected, measured and/or analyzed. Exemplary objects include, but are not limited to, fruits, vegetables, and the like. Sample testing chamber 570 includes exit port 574 including a control valve 575. An extraction liquid storage and collection container 576 is used to collect all extracted liquid that washes over the surfaces of objects 579 as wet foam. Extraction liquid container 576 may be reversibly connectable with a bottom portion 584 of sample testing chamber 570 through conventional techniques such that collected extraction fluid may be removed, packaged and handled for analysis. The wet foam travels from the wet foam distributor 571 in a top portion of the sample testing chamber 570 to a bottom portion 584 of sample testing chamber 570 through a combination of the pressure produced by gas source 547 and gravity. A further fan or vacuum source may be included to facilitate the process.

Figure 6:
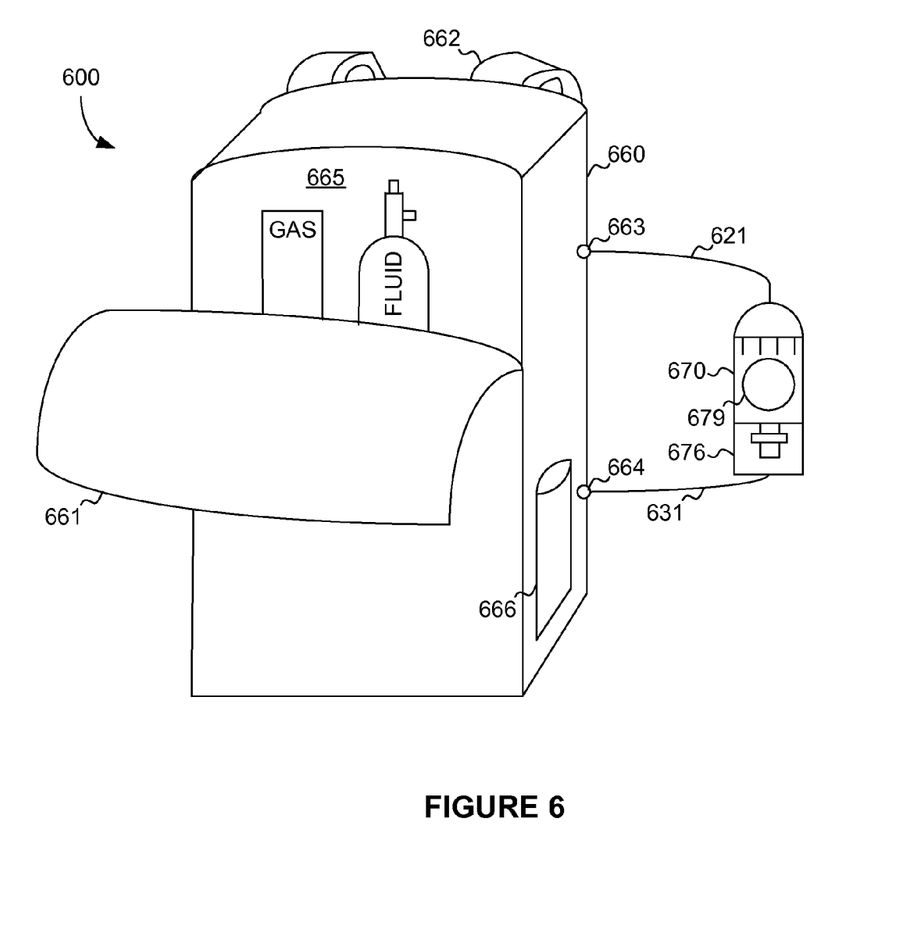
FIG. 6 shows a portable three dimensional surface sampling system, according to an exemplary embodiment of the present invention.

The three dimensional extraction system shown as system 500 in FIG. 5 may also be incorporated into a 15-20 lb portable system, as shown in the exemplary system 600 in FIG. 6. An exemplary configuration of the three dimensional surface extraction system (as shown in, for example, FIG. 5 as system 500) fits within an interior space 665 of a small backpack 660. The cover 661 of the backpack 660 may be opened to change/replace components or collect the extracted fluid. The extraction testing chamber 670 connects to the backpack 660 by a flexible bundle containing the fluid hose 621 (through port 663), vacuum hose 631 (through port 664). The user wears the backpack during use using shoulder straps 662 or other carrying straps. An object 679 with a surface having particles to be extracted is identified and placed within testing chamber 670. The testing chamber 670 is grasped in one hand and the vacuum on/off pressure switch is activated. As the testing chamber 670 washes the surface of the object 679, the collected fluid is stored within liquid container 676. When the object 679 surface has been sampled the foam valve (582 in FIG. 5) is deactivated. The testing chamber 670 may be placed into an external holster or holding pouch 666 for easy future access. The extracted fluid can be drained to an appropriate sample container and prepared for analysis. It is most common to first concentrate the sample in a conventional concentrator system prior to analysis. In other embodiments, it may be possible to incorporate the concentrator and add a further analyzer into the backpack 660 as well.

The embodiments presented and described herein are designed to have modular components which can be easily changed or replaced without affecting other components within the system. For example, extraction wand 410 or testing chamber 670 may be easily replaced with another extraction wand or testing chamber, respectively, after a given sampling has occurred. This prevents cross-contamination while at the same time maintains cost-effectiveness as only components which need to be changed between testing are changed, as needed.

Another optional embodiment would enable the recycling of the extracted fluid such that when the extracted fluid is collected after having been exposed to a surface having particles, the particles are filtered out (using, for example, a hollow fiber filter) and the extracted fluid is then reused on the surface. The sampled particles are then extracted from the filter, further concentrating the sample for further improvement in the ability to detect them. This would allow a very large surface area to be tested with a given volume of extraction fluid without concern that the extraction fluid would run out as it is being collected by the extraction wand.

The embodiments of the device described herein were built using a clear acrylic cylinder, in a cyclone configuration, to catch the sample and reduce the possibility of target particles being lost through the vacuum blower and so that the process could be viewed directly. Passages were drilled in the acrylic to accommodate the liquid flow paths, and fittings were mounted to the ports for tubing connection. Other materials may also be used as would be appreciated by one having ordinary skill in the art after consideration of the present disclosure.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for extracting particles from a surface, the system comprising:
   a source of pressurized liquid containing a liquid;
   a source of gas containing a gas, wherein the source of gas is connected to the source of pressurized liquid such that the gas is dissolved into the liquid;
   an extraction device comprising:
   an outlet port wherein the pressurized liquid having gas dissolved therein is applied as a wet foam to a surface having particles thereon;
   an inlet port wherein the wet foam is extracted from the surface;

a liquid collection reservoir in connection with the inlet port, wherein the wet foam extracted by the inlet port is stored as liquid having particles therein within the collection reservoir; and a testing chamber coupled to the outlet port, wherein the surface is positioned within the testing chamber as the outlet port applies wet foam to the surface and the inlet port collects wet foam from the surface.

2. The system of claim 1, further comprising a surfactant within the pressurized liquid.

3. The system of claim 2, further comprising a buffer within the pressurized liquid.

4. The system of claim 1, wherein the gas comprises carbon dioxide.

5. The system of claim 1, wherein the surface is substantially flat.

6. The system of claim 1, further comprising a source of vacuum connected to the liquid collection reservoir to assist in drawing liquid into the liquid collection reservoir.

7. The system of claim 1, wherein all components are portable within a backpack.

8. The system of claim 1, wherein the surface is contoured.

9. The system of claim 1, wherein the testing chamber comprises a first end which includes the outlet port and a second end which includes the inlet port wherein wet foam is ejected into the testing chamber at the first end and wet foam is collected at the second end.

10. The system of claim 1, wherein the liquid collection reservoir is reversibly connected to the testing chamber.

11. A method for extracting particles from a surface, the method comprising:

providing a source of pressurized liquid;

providing a source of gas, wherein the gas is connected to the pressurized liquid such that the gas is dissolved into the liquid;

applying a wet foam on the surface having particles, the wet foam formed by the gas dissolved in the pressurized liquid being exposed to ambient pressure, the surface being positioned within a testing chamber as the wet foam is applied to the surface;

extracting the wet foam from the surface; and collecting the wet foam as liquid within a reservoir.

12. The method of claim 11, further comprising a surfactant within the pressurized liquid.

13. The method of claim 12, further comprising a buffer within the pressurized liquid.

14. The method of claim 11, wherein the gas comprises carbon dioxide.

15. The method of claim 11, wherein the surface is substantially flat.

16. The method of claim 11, wherein the surface is contoured.

* * * * *